(12) United States Patent
Mire et al.

(10) Patent No.: US 10,736,672 B2
(45) Date of Patent: Aug. 11, 2020

(54) SPINAL IMPLANT SYSTEM AND METHOD

(71) Applicant: Warsaw Orthopedic, Inc, Warsaw, IN (US)

(72) Inventors: David A. Mire, Cordova, TN (US); Joseph Rosenberger, Cordova, TN (US); Michael Simmons, Moscow, TN (US); Christopher I. Shaffrey, Charlottesville, VA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 74 days.

(21) Appl. No.: 15/605,602

(22) Filed: May 25, 2017

(65) Prior Publication Data
US 2018/0338783 A1 Nov. 29, 2018

(51) Int. Cl.
*A61B 17/70* (2006.01)

(52) U.S. Cl.
CPC ...... *A61B 17/7086* (2013.01); *A61B 17/7001* (2013.01); *A61B 17/7049* (2013.01)

(58) Field of Classification Search
CPC ............ A61B 17/7002; A61B 17/7049; A61B 17/7074–17/7091; A61B 17/8605
See application file for complete search history.

(56) References Cited

U.S. PATENT DOCUMENTS

| 4,271,836 A | 6/1981 | Bacal et al. |
| 4,422,451 A | 12/1983 | Kalamchi |
| 5,020,519 A | 6/1991 | Hayes et al. |
| 5,704,937 A | 1/1998 | Martin |
| 5,720,751 A | 2/1998 | Jackson |
| 5,951,564 A | 9/1999 | Schroder |
| 5,966,827 A | 10/1999 | Horvath et al. |
| 6,183,472 B1 | 2/2001 | Lutz |
| 6,440,133 B1 * | 8/2002 | Beale ................. A61B 17/7032 606/104 |
| 6,551,316 B1 | 4/2003 | Rinner et al. |
| 6,716,218 B2 | 4/2004 | Holmes et al. |
| 6,739,068 B1 | 5/2004 | Rinner |
| D566,271 S | 4/2008 | Gao et al. |
| 7,454,939 B2 | 11/2008 | Garner et al. |
| 7,572,281 B2 * | 8/2009 | Runco ................. A61B 17/7086 606/279 |
| 7,611,517 B2 * | 11/2009 | Lim ................... A61B 17/7086 606/86 A |
| 7,621,918 B2 | 11/2009 | Jackson |
| 7,824,411 B2 | 11/2010 | Varieur et al. |

(Continued)

FOREIGN PATENT DOCUMENTS

| AU | 2011218612 B2 | 9/2011 |
| WO | 2013101772 A1 | 7/2013 |
| WO | 2014071161 A1 | 5/2014 |

*Primary Examiner* — Tessa M Matthews
(74) *Attorney, Agent, or Firm* — Sorrell, Lenna & Schmidt, LLP

(57) ABSTRACT

A surgical instrument includes an actuator. A first member is connected with the actuator and is configured to engage a bone fastener that defines a first implant cavity and a second implant cavity. A second member is connected with the actuator and includes an implant engaging surface having a first portion movable along the first implant cavity and a second portion movable along the second implant cavity. Systems, spinal constructs, implants and methods are disclosed.

21 Claims, 13 Drawing Sheets

(56) References Cited

U.S. PATENT DOCUMENTS

| | | |
|---|---|---|
| 7,922,750 B2 | 4/2011 | Trautwein et al. |
| 8,157,809 B2 | 4/2012 | Butters et al. |
| 8,192,438 B2 * | 6/2012 | Garamszegi ....... A61B 17/7086 606/86 A |
| 9,084,642 B2 * | 7/2015 | Peultier .............. A61B 17/7083 |
| 9,949,763 B2 * | 4/2018 | Rezach .............. A61B 17/7032 |
| 2003/0205075 A1 | 11/2003 | Strippgen et al. |
| 2004/0176775 A1 * | 9/2004 | Burkus ................ A61B 17/025 606/90 |
| 2005/0021040 A1 | 1/2005 | Bertagnoli |
| 2005/0149053 A1 | 7/2005 | Varieur et al. |
| 2006/0111712 A1 | 5/2006 | Jackson |
| 2007/0233143 A1 | 10/2007 | Josse et al. |
| 2008/0119862 A1 | 5/2008 | Wicker et al. |
| 2009/0005784 A1 | 1/2009 | Blain et al. |
| 2009/0018593 A1 | 1/2009 | Barrus et al. |
| 2009/0030420 A1 * | 1/2009 | Runco ................ A61B 17/7086 606/99 |
| 2009/0228051 A1 | 9/2009 | Kolb et al. |
| 2009/0228054 A1 * | 9/2009 | Hoffman ............ A61B 17/7086 606/86 A |
| 2009/0281582 A1 | 11/2009 | Villa et al. |
| 2010/0021385 A1 | 1/2010 | Kudo et al. |
| 2010/0262198 A1 | 10/2010 | Braunschweiler |
| 2010/0268279 A1 * | 10/2010 | Gabelberger ...... A61B 17/7035 606/278 |
| 2012/0078308 A1 * | 3/2012 | Dziedzic ............ A61B 17/7086 606/264 |
| 2012/0303062 A1 * | 11/2012 | Amstutz ............ A61B 17/7041 606/267 |
| 2017/0086895 A1 * | 3/2017 | Barra ................ A61B 17/8605 |

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a surgical instrument is provided. The surgical instrument includes an actuator. A first member is connected with the actuator and is configured to engage a bone fastener that defines a first implant cavity and a second implant cavity. A second member is connected with the actuator and includes an implant engaging surface having a first portion movable along the first implant cavity and a second portion movable along the second implant cavity. In some embodiments, systems, spinal constructs, implants and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
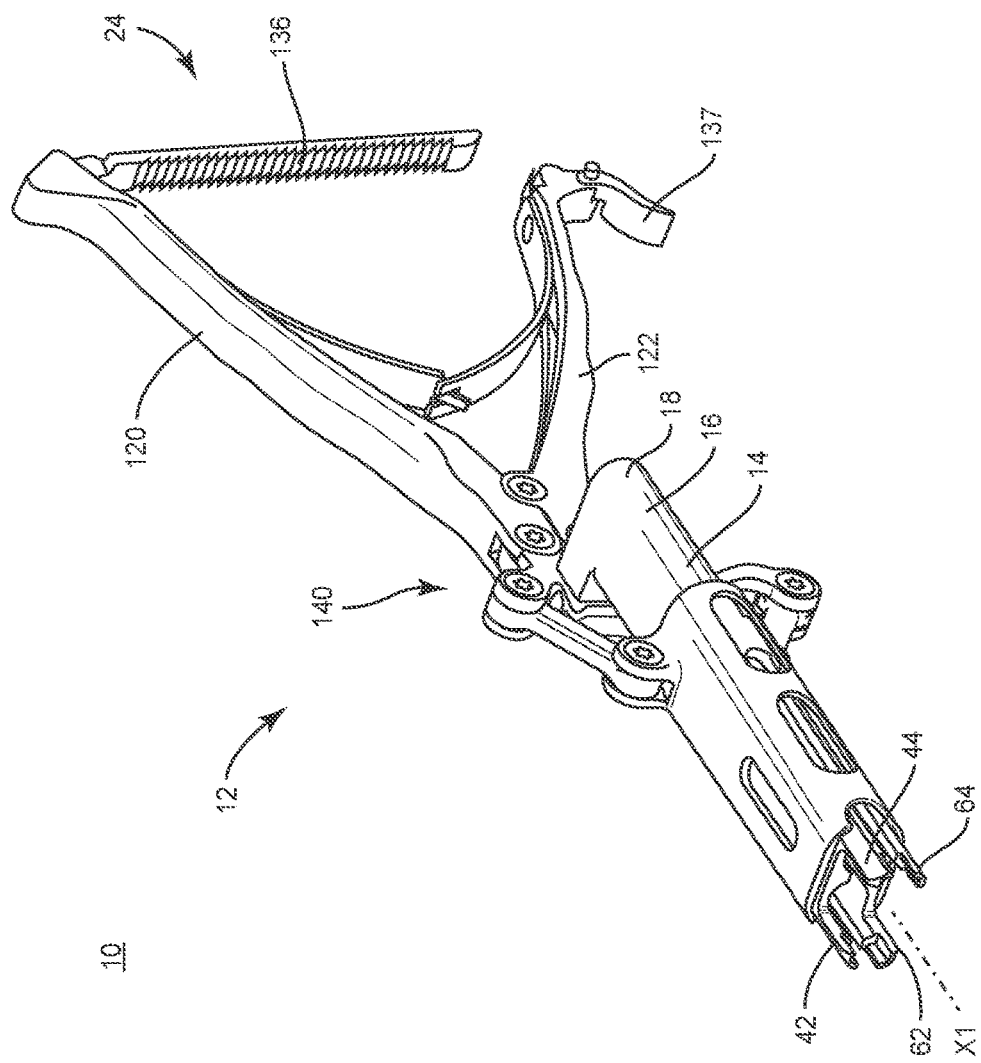
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a surgical instrument, such as, for example, a multi-rod reduction instrument. In some embodiments, the present surgical system includes a surgical instrument that can be employed with spinal constructs including a plurality of spinal rods, for example, three and four rod constructs. In some embodiments, the present surgical system includes a surgical instrument that can be employed with a surgical method that includes complex procedures, such as three column osteotomies.

In some embodiments, the present surgical system includes a surgical instrument that can be employed with a dual headed multi-axial screw (DRMAS). In some embodiments, the present surgical system includes a surgical instrument that can reduce a plurality of spinal rods, for example, two spinal rods with a receiver or receivers of the DRMAS at one time. In some embodiments, the present surgical instrument attaches to a DRMAS screw head and reduces up to two rods at one time. In some embodiments, the present surgical system includes a surgical instrument that can be employed with a surgical method that includes additional fixation.

In some embodiments, the present surgical system includes a fastener having a first implant cavity and a second implant cavity. In some embodiments, the present surgical system includes a spinal construct having a dual rod multi axial screw with a primary rod slot and a secondary rod slot. In some embodiments, the secondary rod slot includes a sagittal adjusting saddle. In some embodiments, the secondary rod slot is configured to accommodate sagittal angulation of a second rod as a screw head position is locked when a first rod is attached. In some embodiments, the sagittal angulation of the secondary rod slot is configured to increase construct performance. In some embodiments, the present surgical system includes a spinal construct having a fastener that supports one or more spinal rods in a configuration to facilitate stabilization of vertebrae.

In some embodiments, the fastener includes a first rod slot aligned with a bone screw shaft and a second rod slot connected with the first slot. In some embodiments, the second rod slot is disposed in a parallel and adjacent orientation relative to the first rod slot. In some embodiments, the second rod slot is disposed in an angled and adjacent orientation relative to the first rod slot. In some embodiments, the second rod slot is disposed in a parallel and offset orientation relative to the first rod slot. In some embodiments, the second rod slot is disposed in an angled and offset orientation relative to the first rod slot.

In some embodiments, the first rod slot and/or the second rod slot can be connected with the bone screw shaft in a multi axial screw configuration, a fixed angle screw configuration or a sagittal adjusting screw configuration. In some embodiments, the fastener includes a reduction head having extended tabs that define the first rod slot and can be connected with a bone screw shaft in a multi axial screw configuration, a fixed angle screw configuration or a sagittal adjusting screw configuration. In some embodiments, the fastener includes a saddle disposed for movement with the first rod slot and/or the second rod slot in a multi axial screw configuration, a fixed angle screw configuration or a sagittal adjusting screw configuration. In some embodiments, the fastener includes a reduction head having extended tabs that define the first rod slot and/or the second rod slot and a saddle disposed for movement with the first rod slot and/or the second rod slot in a multi axial screw configuration, a fixed angle screw configuration or a sagittal adjusting screw configuration.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-10, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a surgical instrument, such as, for example, a spinal rod reducer 12. Reducer 12 is configured as an implant support for connection with a bone fastener, such as, for example, a DRMAS 212 (FIG. 11) for simultaneous reduction of one or multiple spinal rods with DRMAS 212, as described herein.

Reducer 12 includes an inner member 14 having a body 16. Body 16 extends between an end 18 and an end 20 along an axis X1. Body 16 includes an oblong cross section configuration. In some embodiments, all or only a portion of body 16 may have alternate cross section configurations, such as, for example, oval triangular, square, polygonal, irregular, uniform, non-uniform, offset, staggered, and/or tapered.

Figure 7:
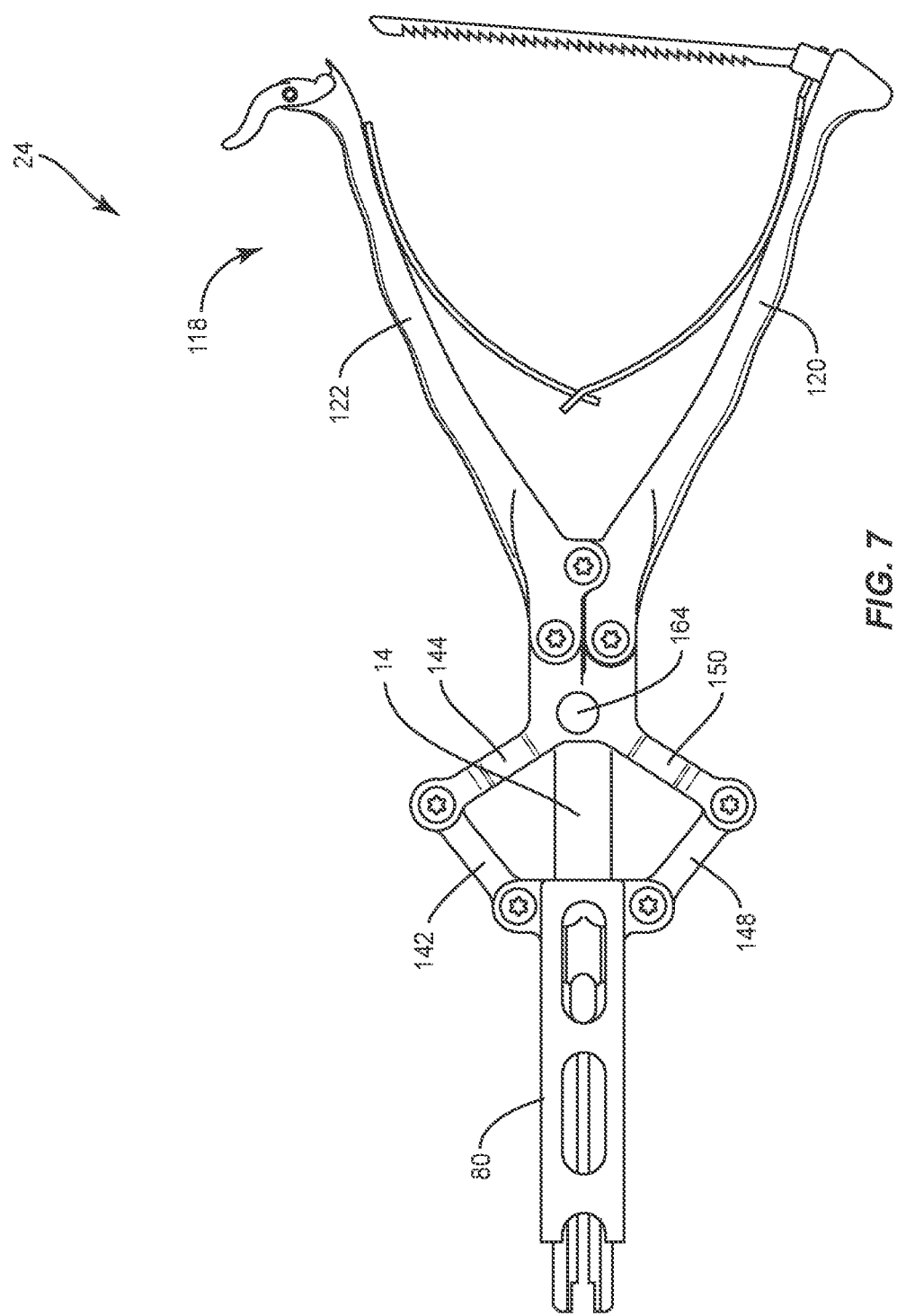
FIG. 7 is a side view of the components shown in FIG. 1.
Figure 8:
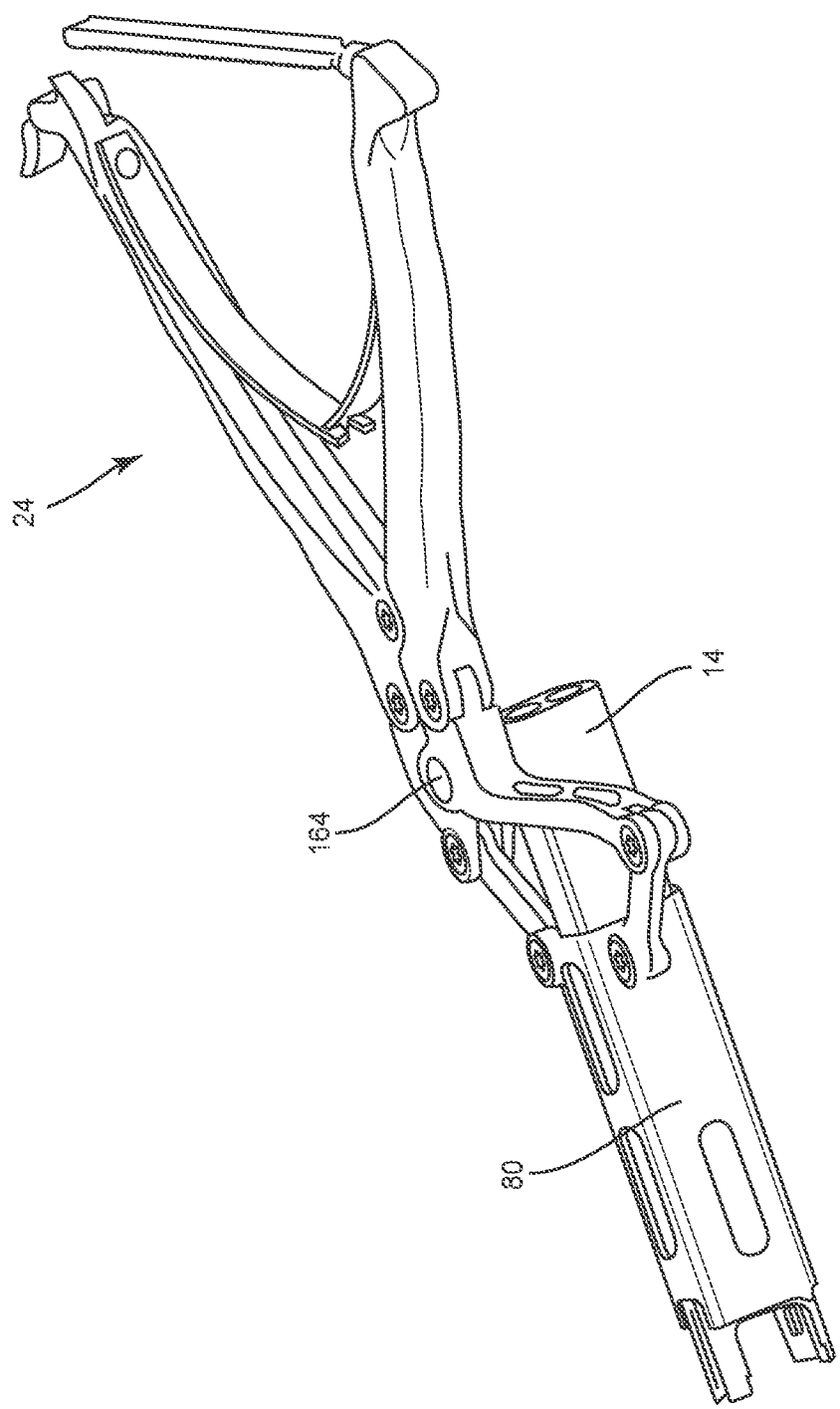
FIG. 8 is a perspective view of the components shown in FIG. 1.
Figure 9:
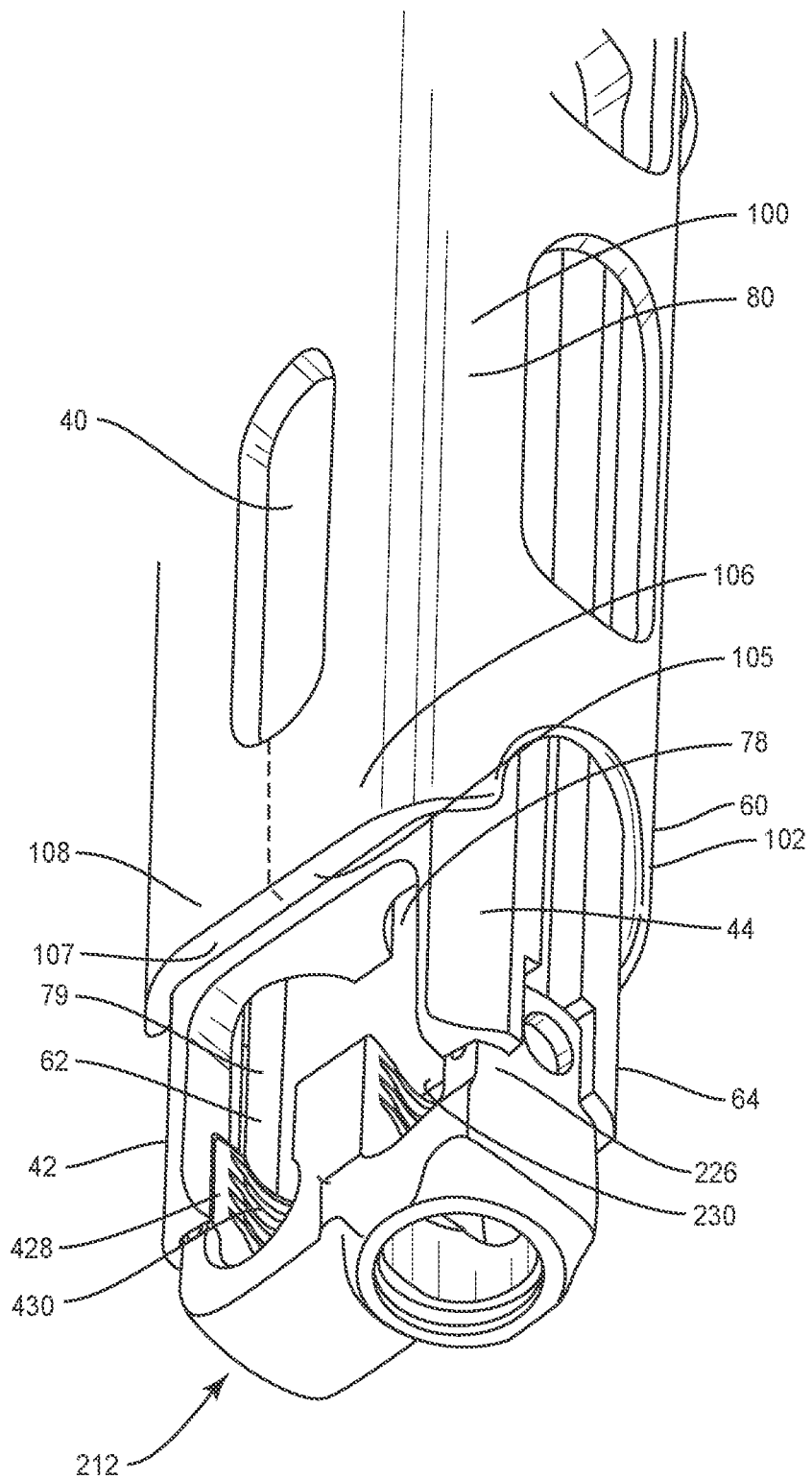
FIG. 9 is a break away view of components of one embodiment of a surgical system in accordance with the principles of the present disclosure.
Figure 10:
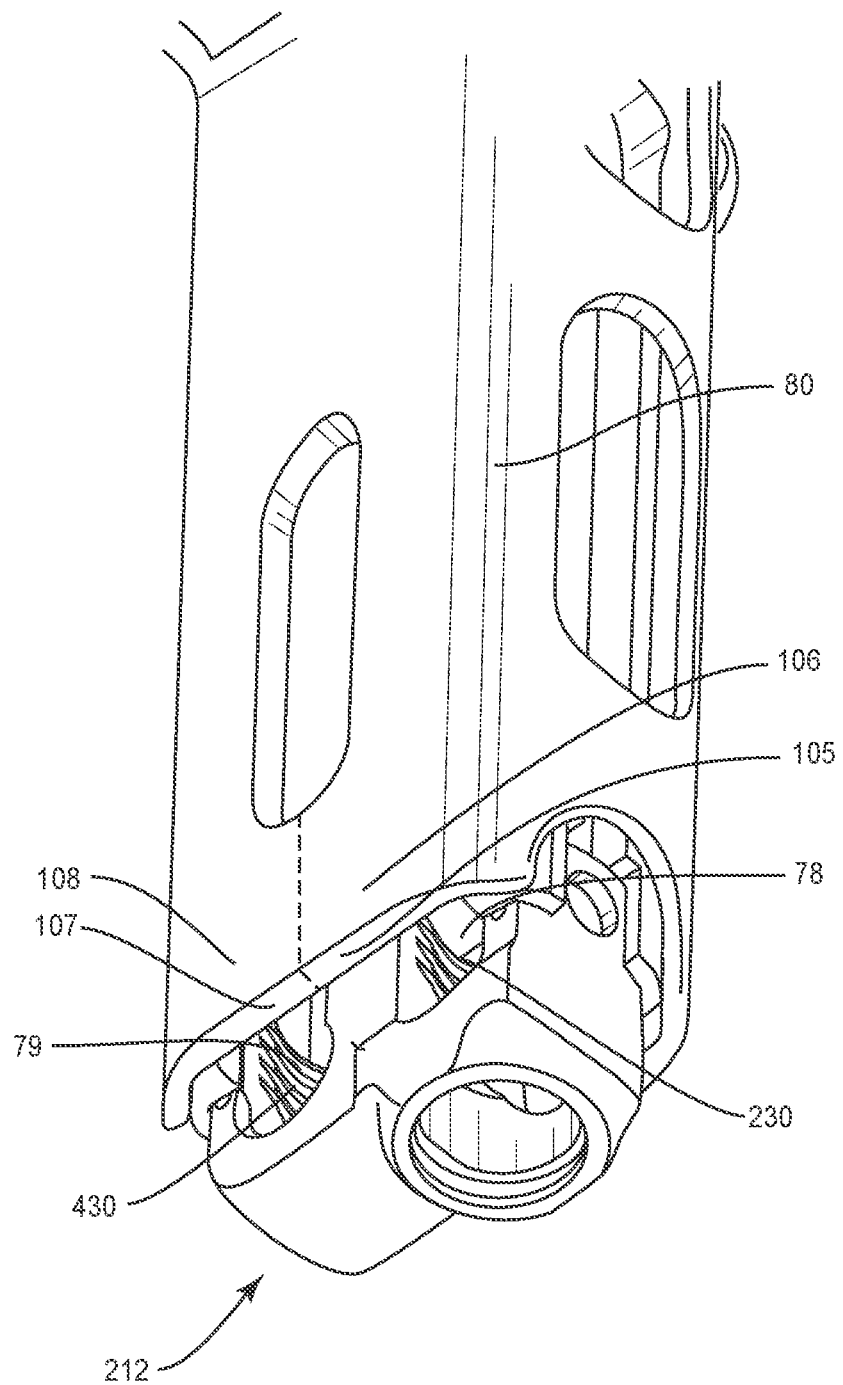
FIG. 10 is a break away view of components of one embodiment of a surgical system in accordance with the principles of the present disclosure.

Member 14 includes a protrusion 22 configured for connection with an actuator 24, as described herein. Protrusion 22 connects actuator 24 with body 16 via a pin 164, as shown in FIGS. 7 and 8, such that linkages of actuator 24 can relatively translate the components of reducer 12 for reduction of one or multiple spinal rods with DRMAS 212, as described herein. Protrusion 22 is connected with actuator 24 to dispose body 16 in an offset orientation relative thereto, which provides access to passageways 32, 36 for guidance of implants and/or components of a spinal construct, for example, a set screw, and/or a surgical instrument, as described herein.

Member 14 includes a surface 30 that defines passageway 32. Member 14 includes a surface 34 that defines passageway 36. Passageways 32, 36 extend relatively parallel in a spaced apart and/or side by side relation. In some embodiments, passageways 32, 36 may be variously configured, such as, for example, uniform, non-uniform, offset, staggered, undulating, arcuate, variable and/or tapered. Passageways 32, 36 include and/or are aligned with rod slots of body 16, as described herein, and/or aligned with rod slots 230, 430 of DRMAS 212, as described herein. Passageways 32, 36 direct and/or guide a surgical instrument, such as, for example, a driver and/or a coupling member, for example, a set screw into engagement with DRMAS 212 to facilitate fixation of spinal rods 350, 352 with DRMAS 212, as described herein.

Figure 2:
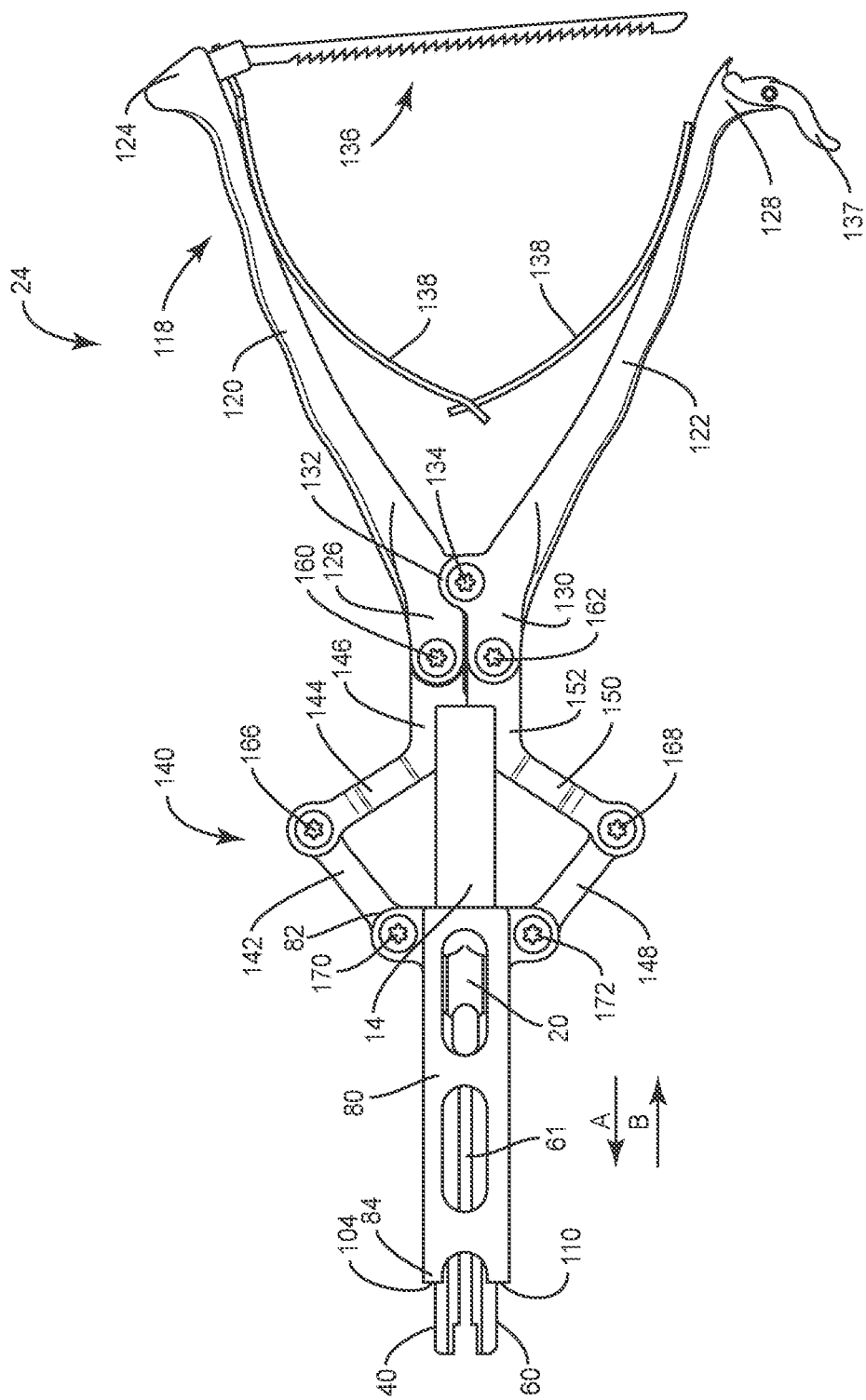
FIG. 2 is a side view of the components shown in FIG. 1.

Member 14 includes an inner extension 40 and an inner extension 60. Extensions 40, 60 are flexible and extend from end 20 of body 16, as shown in FIG. 2. In some embodiments, extension 40 and/or extension 60 flexibly extend from end 20 in a cantilevered configuration. In some embodiments, all or only a portion of extension 40 and/or extension 60 may be alternately configured, such as, for example, uniform, non-uniform, offset, staggered, undulating, arcuate, variable and/or tapered.

Extensions 40, 60 are movable to facilitate capture of DRMAS 212, as described herein. Extensions 40, 60 define rod slots 78, 79, as shown in FIGS. 3, 4, 9 and 10. Slots 78, 79 are open spaces disposed in side by side relation and each slot is configured for disposal of a spinal rod. Rod slot 78 is aligned with and/or includes passageway 32. Rod slot 79 is aligned with and/or includes passageway 36.

For example, slot 78 is configured for disposal of spinal rod 350 and slot 79 is configured for disposal of spinal rod 352 to facilitate simultaneous reduction of rods 350, 352 (FIG. 12) with rod slots 230, 430 of DRMAS 212, as described herein. In some embodiments, rod slots 78, 79 are disposed in parallel relation. In some embodiments, rod slots 78, 79 may be disposed in alternate relative orientations, such as, for example, transverse, perpendicular and/or other angular orientations such as acute or obtuse, coaxial and/or may be offset or staggered. In some embodiments, rod slot 78 and/or rod slot 79 may be variously configured, such as, for example, uniform, non-uniform, offset, staggered, undulating, arcuate, variable and/or tapered. In some embodiments, rod slots 78, 79 may overlap and/or communicate, and/or rod slot 78 and/or rod slot 79 may overlap and/or communicate with passageway 32 and/or passageway 36. In some embodiments, member 14 includes a wall, for example, extending from extension 40 and/or extension 60, disposed between rod slots 78, 79 to separate rod slots 78, 79.

Figure 3:
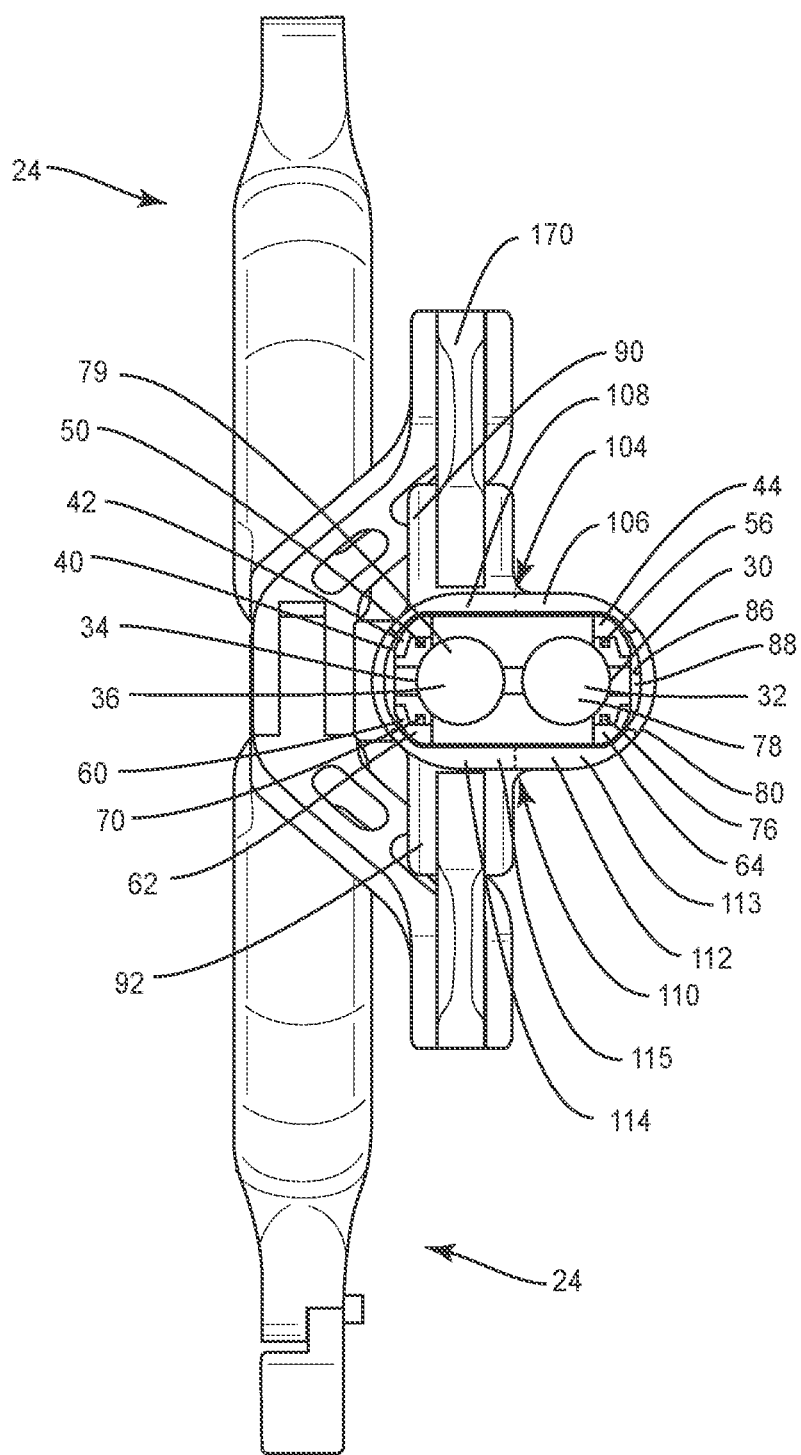
FIG. 3 is an axial view of the components shown in FIG. 1.
Figure 4:
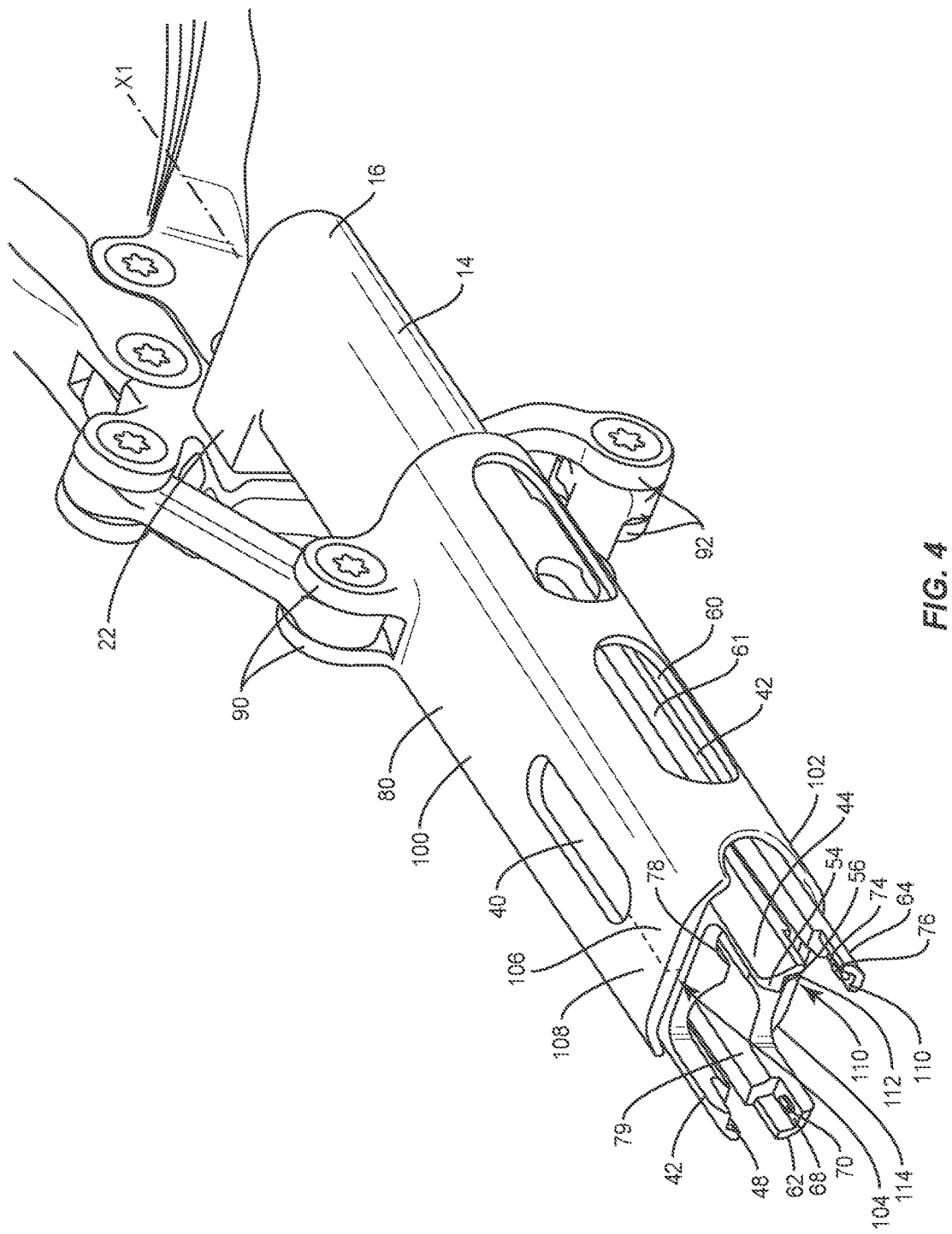
FIG. 4 is a break away view of the components shown in FIG. 1.
Figure 5:
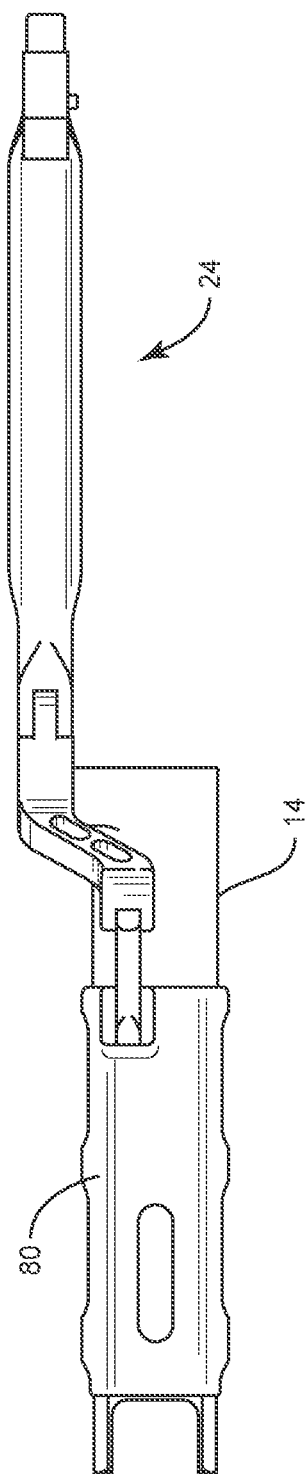
FIG. 5 is a side view of the components shown in FIG. 1.
Figure 6:
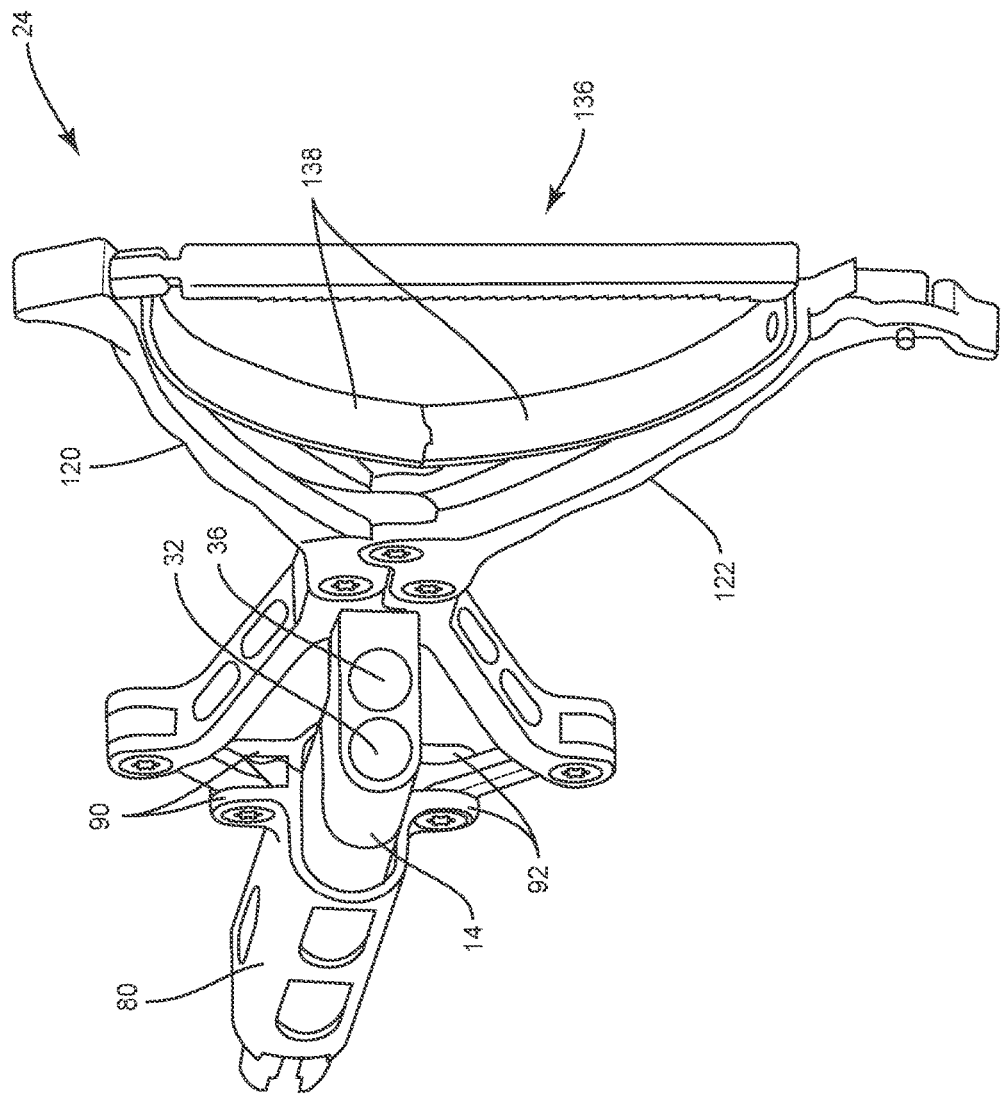
FIG. 6 is a perspective view of the components shown in FIG. 1.

Extension 40 extends parallel to axis X1. Extension 40 includes a leg 42 and a leg 44, as shown in FIGS. 3 and 4. Leg 42 defines a support cavity 48 that is configured for disposal of at least a portion of DRMAS 212. Leg 42 is configured to surround and/or engage a portion of a receiver of DRMAS 212, and defines a tab 50 projecting into cavity 48. Tab 50 releasably captures DRMAS 212. In some embodiments, all or only a portion of leg 42 may have alternate surface configurations to enhance fixation with DRMAS 212, such as, for example, rough, arcuate, undulating, mesh, porous, semi-porous, dimpled and/or textured.

Leg 44 defines a support cavity 54 that is configured for disposal of at least a portion of DRMAS 212. Leg 44 is configured to surround and/or engage a portion of a receiver of DRMAS 212, and defines a tab 56 projecting into cavity 54. Tab 56 releasably captures DRMAS 212. In some embodiments, all or only a portion of leg 44 may have alternate surface configurations to enhance fixation with DRMAS 212, such as, for example, rough, arcuate, undulating, mesh, porous, semi-porous, dimpled and/or textured.

Extension 60 includes a leg 62 and a leg 64. Leg 62 defines a support cavity 68 that is configured for disposal of at least a portion of DRMAS 212. Leg 62 is configured to surround and/or engage a portion of a receiver of DRMAS 212, and defines a tab 70 projecting into cavity 68. Tab 70 releasably captures DRMAS 212. In some embodiments, all or only a portion of leg 62 may have alternate surface configurations to enhance fixation with DRMAS 212, such as, for example, rough, arcuate, undulating, mesh, porous, semi-porous, dimpled and/or textured.

Leg 64 defines a support cavity 74 that is configured for disposal of at least a portion of DRMAS 212. Surface 72 is configured to surround and/or engage a portion of a receiver of DRMAS 212, and defines a tab 76 projecting into cavity 74. Tab 76 releasably captures DRMAS 212. In some embodiments, all or only a portion of leg 64 may have alternate surface configurations to enhance fixation with DRMAS 212, such as, for example, rough, arcuate, undulating, mesh, porous, semi-porous, dimpled and/or textured.

Extension 60 extends parallel to axis X1 in a spaced relation relative to extension 40. Extensions 40, 60 define a lateral slot 61 therebetween. Extensions 40, 60 are resiliently biased to an expanded orientation and are compressed to a contracted orientation to capture DRMAS 212. An outer sleeve 80, as described herein, is translated relative to extensions 40, 60 to engage and compress extensions 40, 60 relative to DRMAS 212 for capture of DRMAS 212. For example, legs 42, 62 are compressed by sleeve 80 to engage and/or capture an arm 226 of receiver 218. Legs 44, 64 are compressed by sleeve 80 to engage and/or capture an arm 428 of receiver 418. In some embodiments, extensions 40, 60 are resiliently biased to a contracted orientation and expandable to capture DRMAS 212. As such, extensions 40, 60 can be translated to engage a head of DRMAS 212, which expands extensions 40, 60 for disposal therewith and the resilient bias contracts legs 42, 62, 44, 64 to capture DRMAS 212.

Reducer 12 includes a member, such as, for example, outer sleeve 80. Sleeve 80 extends between an end 82 and an end 84. Sleeve 80 includes a surface 86 that defines a channel 88, as shown in FIG. 3. Channel 88 is configured for moveable disposal of member 14 such that sleeve 80 is translatable relative to member 14 along axis X1, as described herein. End 82 includes flanges 90, 92 disposed on opposing sides of sleeve 80. Each of flanges 90, 92 define a cavity configured for movable disposal of a portion of handle 24, as described herein.

Sleeve 80 includes a wall 100 and a wall 102 being spaced apart from wall 100. Wall 100 includes portions, such as, for example, segments 106, 108, as shown and separated in phantom in FIGS. 4, 9 and 10. Segments 106, 108 are engageable with spinal rods 350, 352 to facilitate simultaneous reduction of rods 350, 352 (FIG. 12) with rod slots 230, 430 of DRMAS 212, as described herein.

Figure 12:
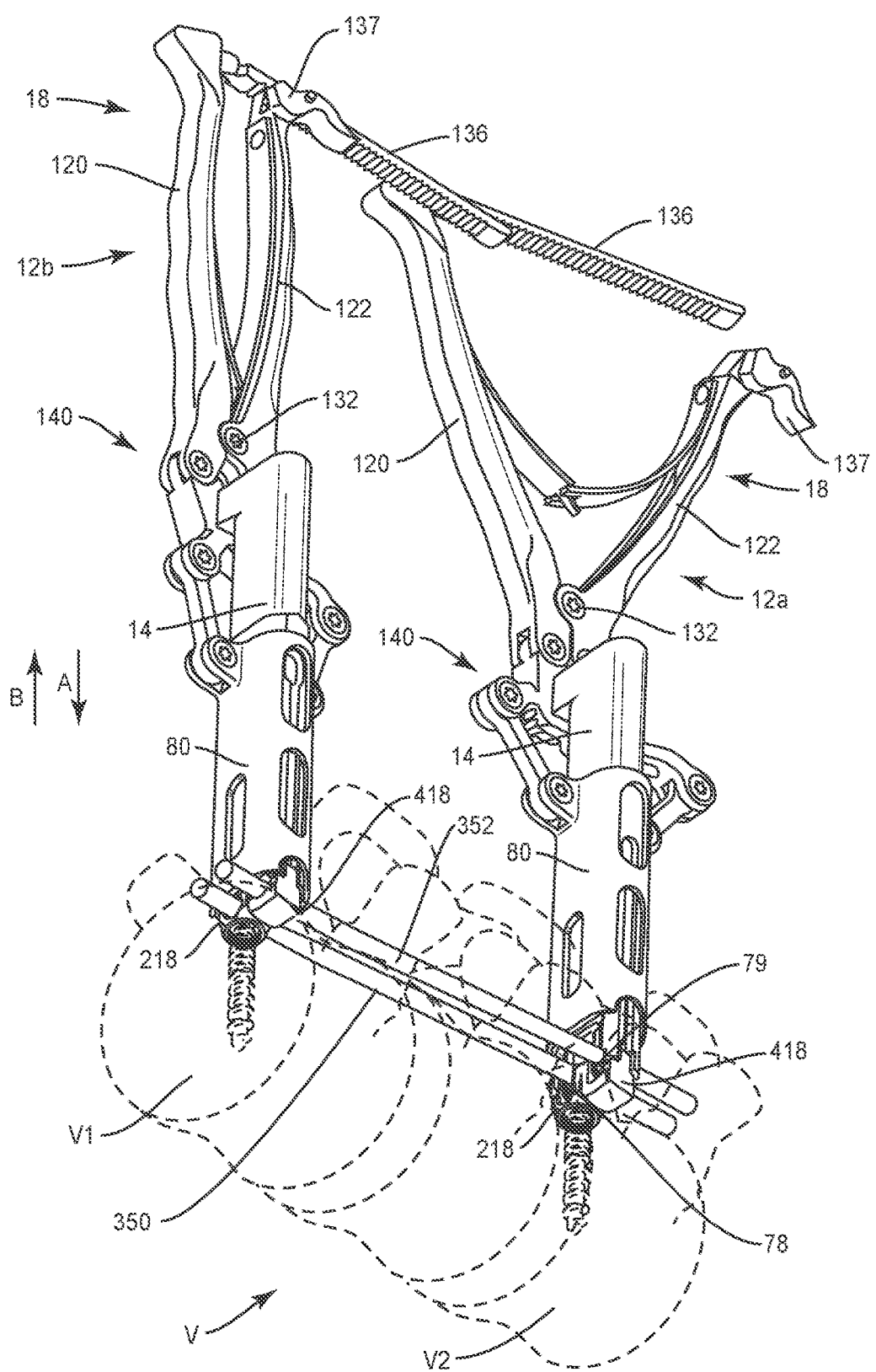
FIG. 12 is a perspective view of components of one embodiment of a surgical system in accordance with the principles of the present disclosure disposed with vertebrae.

Segments 106, 108 define an implant engaging surface 104. Surface 104 includes a planar surface 105 aligned with segment 106 and engageable with a spinal rod, for example, spinal rod 350 (FIG. 12). Surface 105 is configured for axial translation relative to rod slot 78 to reduce spinal rod 350 with rod slot 230. As sleeve 80 translates along slot 78, surface 105 translates into engagement with spinal rod 350 to apply a force to a surface of spinal rod 350 to reduce spinal rod 350 with rod slot 230.

Surface 104 includes a planar surface 107 aligned with segment 108 and engageable with a spinal rod, for example, spinal rod 352 (FIG. 12). Surface 107 is configured for axial translation relative to rod slot 79 to reduce spinal rod 352 with rod slot 430. As sleeve 80 translates along slot 79, surface 107 translates into engagement with spinal rod 352 to apply a force to a surface of spinal rod 352 to reduce spinal rod 352 with rod slot 430. In some embodiments, surfaces 105, 107 and/or segments 106, 108 are disposed in parallel relation. In some embodiments, surfaces 105, 107 and/or segments 106, 108 may be disposed in alternate relative orientations, such as, for example, transverse, perpendicular and/or other angular orientations such as acute or obtuse, coaxial and/or may be offset or staggered. In some embodiments, surfaces 105, 107 and/or segments 106, 108 may be variously configured, such as, for example, uniform, non-uniform, offset, staggered, undulating, arcuate, variable and/or tapered. In some embodiments, surfaces 105, 107 and/or segments 106, 108 may overlap and/or communicate. In some embodiments, extension 40 includes a wall or a cavity disposed between surfaces 105, 107 and/or segments 106, 108.

Wall 102 includes portions, such as, for example, segments 112, 114, as shown in FIGS. 3 and 4. Segments 112, 114 are engageable with spinal rods 350, 352 to facilitate simultaneous reduction of rods 350, 352 (FIG. 12) with rod slots 230, 430 of DRMAS 212, as described herein. Segment 112 is aligned with segment 106 and segment 114 is aligned with segment 108 along a transverse orientation and/or plane, relative to axis X1. As such, segments 112, 106 are simultaneously engageable with spinal rod 350 and/or segments 114, 108 are simultaneously engageable with spinal rod 352 to facilitate simultaneous reduction, as described herein. In some embodiments, sleeve 80 includes only one of walls 100, 102. In some embodiments, only one of walls 100, 102 engage spinal rods 350, 352.

Segments 112, 114 define an implant engaging surface 110. Surface 110 includes a planar surface 113, as shown in FIG. 3, aligned with segment 112 and engageable with a spinal rod, for example, spinal rod 350 (FIG. 12). Surface 113 is configured for axial translation relative to rod slot 78 to reduce spinal rod 350 with rod slot 230. As sleeve 80 translates along slot 78, surface 113 translates into engagement with spinal rod 350 to apply a force to a surface of spinal rod 350 to reduce spinal rod 350 with rod slot 230.

Surface 110 includes a planar surface 115, as shown in FIG. 3, aligned with segment 114 and engageable with a spinal rod, for example, spinal rod 352 (FIG. 12). Surface 115 is configured for axial translation relative to rod slot 79 to reduce spinal rod 352 with rod slot 430. As sleeve 80 translates along slot 79, surface 115 translates into engagement with spinal rod 352 to apply a force to a surface of spinal rod 352 to reduce spinal rod 352 with rod slot 430. In some embodiments, surfaces 113, 115 and/or segments 112, 114 are disposed in parallel relation. In some embodiments, surfaces 113, 115 and/or segments 112, 114 may be disposed in alternate relative orientations, such as, for example, transverse, perpendicular and/or other angular orientations such as acute or obtuse, coaxial and/or may be offset or staggered. In some embodiments, surfaces 113, 115 and/or segments 112, 114 may be variously configured, such as, for example, uniform, non-uniform, offset, staggered, undulating, arcuate, variable and/or tapered. In some embodiments, surfaces 113, 115 and/or segments 112, 114 may overlap and/or communicate. In some embodiments, extension 60 includes a wall or a cavity disposed between surfaces 113, 115 and/or segments 112, 114.

Actuator 24 includes a handle 118 having an arm 120 and an arm 122. Arm 120 extends between an end 124 and an end 126. Arm 122 extends between an end 128 and an end 130. Arm 120 is connected to arm 122 via a pivot, which includes a hinge 132. Arm 122 is configured to rotate relative to arm 120 between an open configuration and a closed configuration, as shown in FIG. 12. Hinge 132 is centrally disposed between arms 120, 122 and configured to facilitate rotation of arm 122 relative to arm 120, and arms 120, 122 relative to axis X1. In some embodiments, hinge 132 may be variously configured, such as, for example, pin, post, screw, living hinge, ratchet and/or concentric parts. Hinge 132 includes a central post 134 that facilitates rotation of arms 120, 122 and pivotal movement and relative rotation therebetween. In some embodiments, handle 118 includes arms 120, 122 disposed in a plier configuration.

Arms 120, 122 include a ratchet 136 disposed adjacent ends 124, 128. Ratchet 136 includes a plurality of teeth engageable with a latch 137 to releasably fix relative position of arms 120, 122. Latch 137 is lockable with ratchet 136 to fix arms 120, 122 position for selectively orienting sleeve 80 relative to member 14, as described herein. For example, latch 137 is locked with teeth of ratchet 136 to releasably fix reduction distance or depth of spinal rods 350, 352 to rod slots 78, 79 and/or DRMAS 212. Arms 120, 124 are resiliently biased to an open configuration by spring arms 138. In some embodiments, arms 120, 122 are freely movable without bias. In some embodiments, arms 120, 122 are non-lockable and freely adjustable such that selective orientation of sleeve 80 relative to member 14 is freely adjustable.

Ends 126, 130 of arms 120, 122 are connected with a linkage 140, as described herein. In some embodiments, the cross section and/or overall configuration of arm 120 and/or arm 122 may be variously configured, such as, for example, round, oval, oblong, square, rectangular, polygonal, irregular, uniform, non-uniform, offset, staggered, tapered, consistent or variable. In some embodiments, arm 120 and/or arm 122 may include an outer gripping surface configured for gripping by a hand of a practitioner. The gripping surface may be, such as, for example, rough, arcuate, undulating, mesh, porous, semi-porous, dimpled and/or textured.

Linkage 140 is configured to axially translate sleeve 80 relative to member 14, in the directions shown by arrows A and B in FIG. 2. Linkage 140 includes extensions 142, 144, 146, 148, 150, 152. Extensions 146, 152 are pivotably connected to ends 126, 130 by pivots 160, 162. Extensions 144, 150 are pivotably connected with member 14 by a pivot 164, as shown in FIG. 7. Extensions 142, 148 are pivotably connected with extensions 144, 150 via pivots 166, 168. Extensions 142, 148 are pivotably connected with sleeve 80 via pivots 170, 172. Pivots 170, 172 are connected with flanges 90, 92 by, for example, screw, friction fit, pressure fit, locking protrusion/recess, locking keyway and/or adhesive. In some embodiments, pivots 160, 162, 164, 166, 168, 170, 172 may include, for example, a pin, post, screw, living hinge, ratchet and/or concentric parts. In some embodiments, the cross section and/or overall configuration of extensions 142, 144, 146, 148, 150 and 152 may be variously configured, such as, for example, round, oval, oblong, square, rectangular, polygonal, irregular, uniform, non-uniform, offset, staggered, tapered, consistent or variable.

Arms 120, 122 are moveable between an open configuration, as shown by reducer 12a in FIG. 12, and a closed configuration, as shown by reducer 12b in FIG. 12. Handle 118 is manipulated for rotation within a range of movement between the open configuration and the closed configuration. Arms 120, 122 pivot about hinge 132 such that the components of linkage 140 rotate about pivots 160, 162, 134, 166, 168. Extensions 142, 144, 148, 150 drive sleeve 80 axially, in the direction shown by arrow A in FIG. 2, to an extended or reduction position such that surfaces 104, 110 engage spinal rods 350, 352. Axial translation of sleeve 80 relative to member 14 cause segments 112, 106 to simultaneously engage spinal rod 350 and/or segments 114, 108 to simultaneously engage spinal rod 352 for simultaneous reduction, as described herein. Sleeve 80 is selectively positionable relative to member 14 and/or rods 350, 352 are selectively positioned and/or reduced with rod slots 78, 79 and/or DRMAS 212. Ratchet 136 and latch 137 are releasably lockable to fix a relative position of arms 120, 122 in a selected orientation, as described herein. In some embodiments, a set screw can be delivered via passageways 32, 36 for engagement with DRMAS 212 to fix spinal rods 350, 352 with DRMAS 212, as described herein.

For example, upon selective reduction of rods 350, 352, as described herein, latch 137 is disengaged from ratchet 136 to release surfaces 104, 110 from spinal rods 350, 352. Handle 118 is manipulated such that spring arms 138 bias and rotate arms 120, 122 into the open configuration. Arms 120, 122 pivot about hinge 132 such that the components of linkage 140 rotate and draw sleeve 80 in a proximal direction. Sleeve 80 translates axially, in the direction shown by arrow B in FIG. 2, to a retracted or non-reduced position. Sleeve 80 axially translates relative to member 14 and segments 112, 106 and/or 114, 108 simultaneously disengage from spinal rods 350 and/or 352.

DRMAS 212 includes a head 214 and a shaft 220. Head 214 and shaft 220 are attached in a multi-axial screw configuration. In some embodiments, head 214 is selectively moveable along a plurality of axes relative to shaft 220 in a multi-axial configuration to accommodate connection with one or more spinal rods, as described herein. In some embodiments, the selected movement includes movement through one or more of transverse, vertical, horizontal, diagonal, coronal and/or sagittal planes of a body. In some embodiments, head 214 is disposed in a fixed orientation relative to shaft 220.

Figure 11:
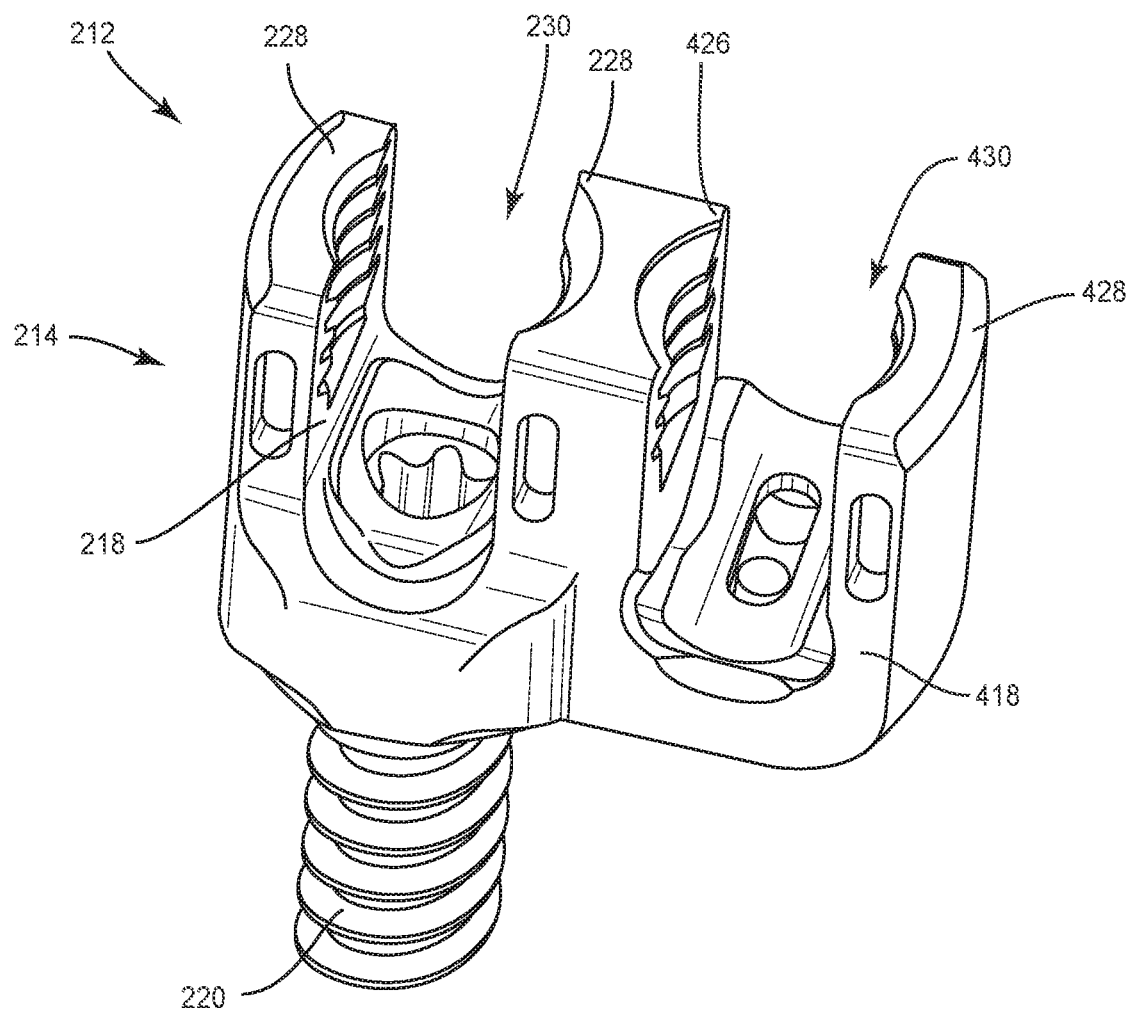
FIG. 11 is a perspective view of components of one embodiment of a surgical system in accordance with the principles of the present disclosure.

Head 214 defines a receiver 218 that is disposed in axial alignment with a head or connecting portion of shaft 220. Receiver 218 includes an arm 226 and a portion 228 of an intermediate arm of head 214. Arm 226 and portion 228 are spaced apart. Arm 226 and portion 228 define an implant cavity, such as, for example, rod slot 230 therebetween. Rod slot 230 is configured for top loading of a spinal implant, such as, for example, a spinal rod 350, as shown in FIG. 11. In some embodiments, rod slot 230 is configured for side loading or has a closed configuration. In some embodiments, at least one of the outer surfaces and the side surfaces of arm 226 and portion 228 have at least one recess or cavity therein configured to receive an insertion tool, compression instrument and/or surgical instruments, for example, legs 44, 64, as described herein, for capturing and/or manipulating DRMAS 212. Receiver 218 includes thread forms configured for engagement with a coupling member, such as, for example, a set screw (not shown) to retain, for example, spinal rod 350 within rod slot 230.

Head 214 includes a receiver 418, similar to receiver 218 described herein. Receiver 418 includes arm 428 and a portion 426 of the intermediate arm of head 214. Arm 428 and portion 426 are spaced apart. Arm 428 and portion 426 define an implant cavity, such as, for example, rod slot 430 therebetween. Rod slot 430 is configured for top loading of a spinal implant, such as, for example, a spinal rod 352. In some embodiments, rod slot 430 is configured for side loading or has a closed configuration. In some embodiments, at least one of the outer surfaces and the side surfaces of arm 428 and portion 426 have at least one recess or cavity therein configured to receive an insertion tool, compression instrument and/or surgical instruments, for example, legs 42, 62, as described herein, for capturing and/or manipulating DRMAS 212. In some embodiments, shaft 220 is selectively movable relative to receiver 418 through an angular range and disposable at a selected angle relative to receiver 418. Receiver 418 includes thread forms configured for engagement with a coupling member, such as, for example, a set screw (not shown) to retain, for example, spinal rod 352 within rod slot 430. In some embodiments, portion 426 is configured for disposal of a saddle configured for moveable disposal relative to receiver 418 in a plane, such as, for example, a sagittal plane of a body and/or vertebrae.

Shaft 220 is configured to penetrate tissue, such as, for example, bone. The head or connecting portion of shaft 220 is disposed in alignment with receiver 218 such that receiver 418 is offset from shaft 220. In some embodiments, shaft 220 includes a threaded surface to facilitate engagement with tissue. In some embodiments, head 214 is monolithically formed with shaft 220. In some embodiments, head 214 is attached with shaft 220 such that bone fastener 212 comprises, for example, a sagittal angulation screw, pedicle screw, mono-axial screw, uni-planar screw, facet screw, fixed screw, tissue penetrating screw, conventional screw, expanding screw, wedge, anchor, staple, nail and/or post. In some embodiments, the head or connecting portion of shaft 220 may be alternatively aligned with intermediate portions of head 14 and/or adjacent receiver 418.

In some embodiments, spinal implant system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels.

In assembly, operation and use, spinal implant system 10, similar to the systems and methods described herein, is employed with a surgical procedure, such as, for example, a correction treatment of an applicable condition or injury of an affected section of a spinal column and adjacent areas within a body. Spinal implant system 10 may be completely or partially revised, removed or replaced.

Figure 13:
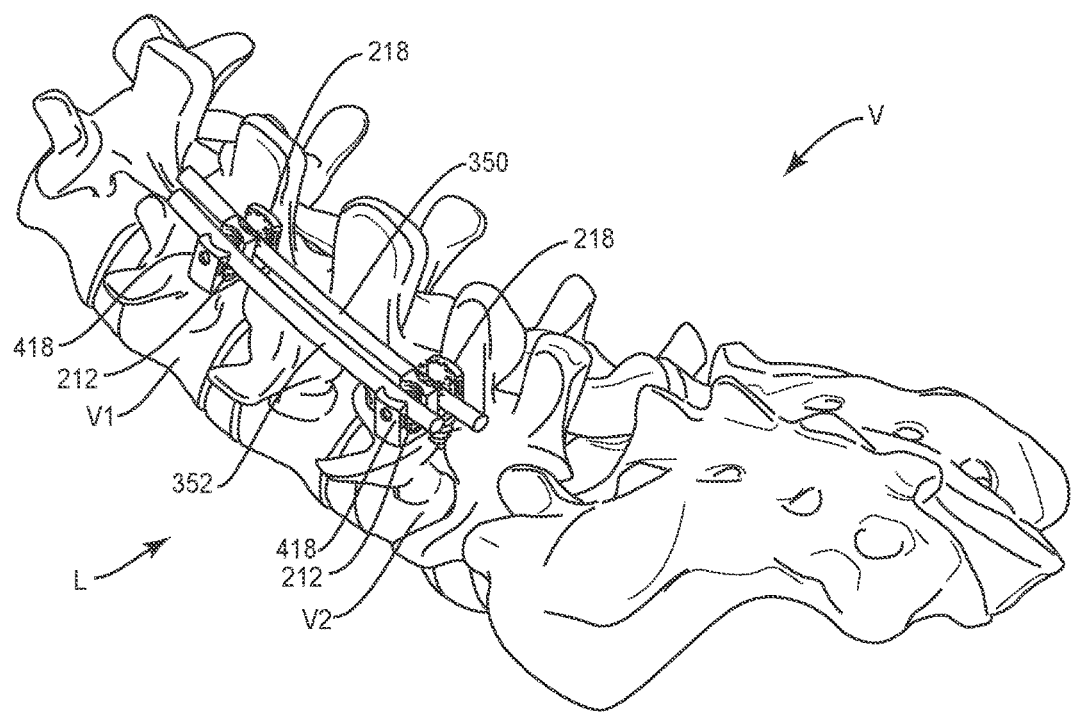
FIG. 13 is a perspective view of components of one embodiment of a surgical system in accordance with the principles of the present disclosure disposed with vertebrae.

In use, to treat a selected section of vertebrae V, including vertebrae V1, V2, as shown in FIGS. 12 and 13, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

One or more DRMAS 212, as described herein, are engaged with vertebrae V along a lateral side L of vertebrae V. Each shaft 220 is manipulated to drive, torque, insert or otherwise connect a DRMAS 212 with vertebrae V. One or more reducers 12, as described herein, are disposed adjacent the surgical site and manipulated for engagement with each DRMAS 212, as described herein. Legs 42, 62, 44, 64, as described herein, are disposed adjacent receivers 218, 418 and engaged with receivers 218, 418. Legs 42, 62, 44, 64 slide over receivers 218, 418 and contract such that the projections of legs 42, 62, 44, 64 engage the cavities of receivers 218, 418, as described herein, to fix reducer 12a with DRMAS 212 attached with vertebra V2 and reducer 12b with DRMAS 212 attached with vertebra V1. As such, member 14 captures each DRMAS 212, as described herein.

Spinal rod 350 is delivered along the surgical pathway to the surgical site adjacent vertebrae V. Spinal rod 350 is disposed with slot 78 of each reducer 12a and reducer 12b. Spinal rod 352 is delivered along the surgical pathway to the surgical site adjacent vertebrae V. Spinal rod 352 is disposed with slot 79 of each reducer 12a and reducer 12b.

Each handle 118 is manipulated from the open configuration to rotate arms 120, 122 into the closed configuration, as described herein, such that the components of linkage 140 axially translate sleeve 80, in the direction shown by arrow A in FIG. 12, to an extended or reduction position. As shown in FIG. 12, reducer 12a is disposed in the open configuration and reducer 12b is disposed in the closed configuration. Handle 118 is manipulated and surfaces 104, 110 of each reducer 12a and reducer 12b engage spinal rods 350, 352, as described herein. As sleeve 80 axially translates relative to member 14, segments 112, 106 simultaneously engage spinal rod 350 and/or segments 114, 108 simultaneously engage spinal rod 352 for simultaneous reduction of rods 350, 352 with rod slots 230, 430.

Handle 118 is manipulated and sleeve 80 is selectively positionable relative to member 14 and/or rods 350, 352 are selectively positioned and/or reduced with rod slots 78, 79 and/or DRMAS 212. For example, reducer 12b reduces rods 350, 352 with rod slots 230, 430 of DRMAS 212 attached with vertebra V1, as described herein. Ratchet 136 and latch 137 are releasably lockable to fix a relative position of arms 120, 122 in a selected orientation, as described herein. Sleeve 80 is releasably fixed relative to member 14 in a selected reduction of rods 350, 352 with DRMAS 212 attached with vertebra V1.

With ratchet 136 of reducer 12b locked to fix reduction position of rods 350, 352 with DRMAS 212 attached with vertebra V1, reducer 12a reduces rods 350, 352 with rod slots 230, 430 of DRMAS 212 attached with vertebra V2, as described herein. In some embodiments, a set screw can be delivered via passageways 32, 36 for engagement with each DRMAS 212 to fix spinal rods 350, 352 with DRMAS 212, as described herein. A surgical driver can be guided through passageways 32, 36 for engaging set screws for fixation with spinal rods 350, 352 and DRMAS 212.

Upon selective reduction of rods 350, 352 with DRMAS 212 attached with vertebra V1, V2, latch 137 is disengaged from ratchet 136 to release surfaces 104, 110 of reducers 12a, 12b from spinal rods 350, 352. Handle 118 is manipulated such that spring arms 138 bias and rotate arms 120, 122 into the open configuration. Sleeve 80 translates axially, in the direction shown by arrow B in FIG. 12, to a retracted or non-reduced position. Sleeve 80 axially translates relative to member 14 and segments 112, 106, 114, 108 simultaneously disengage spinal rods 350, 352. Legs 42, 62, 44, 64 are detached from receivers 218, 418.

In some embodiments, spinal implant system 10 includes one or more DRMAS 212 and spinal rods 350, 352 (not shown) delivered along the surgical pathway to the surgical site adjacent a contra-lateral side of vertebrae V. The one or more DRMAS 212 and spinal rods 350, 352 are connected with the contra-lateral side of vertebrae V, similar to lateral side L described herein. In some embodiments, the spinal constructs of spinal implant system 10, as described herein, are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
   a bone fastener including a first arm, a second arm and a third arm, the first arm and the second arm defining a first implant cavity, the third arm and the second arm defining a second implant cavity;
   an actuator;
   a first member connected with the actuator and being configured to engage the bone fastener, the first member defining a first passageway aligned with the first implant cavity and a second passageway aligned with the second implant cavity; and
   a second member connected with the actuator and including an implant engaging surface having a first portion movable along the first implant cavity and a second portion movable along the second implant cavity.

2. A surgical system as recited in claim 1, wherein the implant engaging surface extends in a transverse orientation relative to the first member to engage at least one spinal rod.

3. A surgical system as recited in claim 1, wherein the implant engaging surface includes a planar surface and extends in a transverse orientation relative to the first member.

4. A surgical system as recited in claim 1, wherein the implant engaging surface is configured to simultaneously engage a spinal rod disposed with the first implant cavity and a spinal rod disposed with the second implant cavity.

5. A surgical system as recited in claim 1, wherein the second member has a wall including the implant engaging surface such that the first portion is aligned with the second portion.

6. A surgical system as recited in claim 1, wherein the second member has a first wall and a second wall spaced apart from the first wall, the walls including the implant engaging surface.

7. A surgical system as recited in claim 6, wherein the first portion is aligned with the second portion.

8. A surgical system as recited in claim 1, wherein the first member includes spaced apart inner extensions and the second member includes an outer sleeve that axially translates relative to the extensions to engage at least one spinal rod.

9. A surgical system as recited in claim 1, wherein the first member includes extensions configured to releasably capture the bone fastener.

10. A surgical system as recited in claim 1, wherein the first member includes movable extensions configured to releasably capture the first arm and the third arm.

11. A surgical system as recited in claim 1, wherein the actuator includes a linkage connected with the second member to axially translate the second member relative to the first member.

12. A surgical system as recited in claim 1, wherein the actuator includes a handle connected with a linkage that axially translates the second member relative to the first member.

13. A surgical system as recited in claim 12, wherein the handle is resiliently biased to an open configuration.

14. A surgical system as recited in claim 12, wherein the handle includes a ratchet.

15. A surgical system as recited in claim 1, further comprising a first spinal rod disposed with the first implant cavity and a second spinal rod disposed with the second implant cavity, wherein the implant engaging surface is configured to simultaneously engage the first spinal rod and the second spinal rod.

16. A surgical system comprising:
   a bone fastener including a first arm, a second arm and a third arm, the first arm and the second arm defining a first implant cavity, the third arm and the second arm defining a second implant cavity;
   an actuator including a linkage;
   a member connected with the actuator, the member comprising spaced apart extensions configured to engage the bone fastener, the member defining a first passageway aligned with the first implant cavity and a second passageway aligned with the second implant cavity; and
   a sleeve connected with the linkage, the sleeve including a first wall and a second wall, the walls being axially translatable along the implant cavities to engage a spinal rod disposed with the first implant cavity and a spinal rod disposed with the second implant cavity.

17. A surgical system as recited in claim 16, wherein the bone fastener includes a first arm and a second arm that define the first implant cavity, and a third arm and the second arm define the second implant cavity, the extensions being contractible to releasably capture the first arm and the third arm.

18. A surgical system as recited in claim 16, wherein the actuator includes a handle connected with the linkage, the handle including a lock to dispose the sleeve in a selected position relative to the bone fastener.

19. A surgical system as recited in claim 16, wherein the first wall includes a first portion of an implant engaging surface and the second wall includes a second portion of the implant engaging surface, the implant engaging surface configured to simultaneously engage the spinal rod disposed with the first implant cavity and the spinal rod disposed with the second implant cavity.

20. A surgical system as recited in claim 16, wherein the first wall is spaced apart from the second wall.

21. A spinal implant system comprising:
- a surgical instrument including an actuator connected with a first member and a second member, the second member including an implant engaging surface;
- a bone fastener including a head having a first receiver that defines an implant cavity and a second receiver that defines an implant cavity, and a shaft engageable with tissue;
- a first spinal rod disposable with the first receiver; and
- a second spinal rod disposable with the second receiver, the implant engaging surface having a first portion being movable along the first receiver to engage the first spinal rod and a second portion being movable along the second receiver to engage the second spinal rod.

* * * * *